(12) United States Patent
Keck

(10) Patent No.: US 9,457,115 B2
(45) Date of Patent: Oct. 4, 2016

(54) RECYCLABLE INDICATOR TAPE FOR STERILIZATION

(71) Applicant: Avent, Inc., Alpharetta, GA (US)

(72) Inventor: Laura E. Keck, Alpharetta, GA (US)

(73) Assignee: Avent, Inc., Alpharetta, GA (US)

( * ) Notice: Subject to any disclaimer, the term of this patent is extended or adjusted under 35 U.S.C. 154(b) by 77 days.

(21) Appl. No.: 14/278,049

(22) Filed: May 15, 2014

(65) Prior Publication Data

US 2014/0356963 A1 Dec. 4, 2014

Related U.S. Application Data

(60) Provisional application No. 61/829,471, filed on May 31, 2013.

(51) Int. Cl.
*G01N 31/22* (2006.01)
*A61L 2/28* (2006.01)

(52) U.S. Cl.
CPC ............... *A61L 2/28* (2013.01); *G01N 31/226* (2013.01)

(58) Field of Classification Search
CPC .............................. G01N 31/226; A61L 2/28
USPC ...................... 422/1, 26–29; 436/1
See application file for complete search history.

(56) References Cited

U.S. PATENT DOCUMENTS

| | | | | |
|---|---|---|---|---|
| 1,843,234 A * | 2/1932 | Karnes | ................... | G01N 31/22 116/201 |
| 2,241,384 A | 5/1941 | Bateman et al. | | |
| 2,998,306 A * | 8/1961 | Huyck | ................. | G01N 31/221 116/DIG. 14 |
| 3,078,182 A | 2/1963 | Crone, Jr. et al. | | |
| 3,698,296 A * | 10/1972 | Heuser | ................... | B65C 11/02 250/461.1 |
| 3,981,683 A | 9/1976 | Larsson et al. | | |
| 3,992,154 A * | 11/1976 | Whitbourne | ............... | A61L 2/28 422/34 |
| 4,015,937 A * | 4/1977 | Miyamoto | ................ | A61L 2/28 116/206 |
| 4,097,236 A * | 6/1978 | Daly | ....................... | B65D 75/30 206/439 |
| 4,188,437 A | 2/1980 | Rohowetz | | |
| 4,436,819 A * | 3/1984 | Manning | ................... | A61L 2/28 422/429 |
| 4,753,188 A * | 6/1988 | Schmoegner | .......... | G01K 11/06 116/207 |
| 4,898,762 A | 2/1990 | Brown et al. | | |
| 4,937,115 A * | 6/1990 | Leatherman | ............... | B32B 5/18 428/315.5 |
| 5,057,433 A | 10/1991 | Douglas | | |
| 5,258,065 A * | 11/1993 | Fujisawa | ................... | A61L 2/28 436/1 |
| 5,332,548 A * | 7/1994 | Moore | ................. | G01N 31/223 422/421 |
| 5,397,614 A | 3/1995 | Patnode et al. | | |
| 5,460,880 A | 10/1995 | Patnode et al. | | |
| 5,518,763 A | 5/1996 | Patnode et al. | | |
| 5,590,777 A * | 1/1997 | Weiss | .................... | A61B 19/026 206/439 |
| 5,641,567 A | 6/1997 | Brown et al. | | |
| 5,780,098 A | 7/1998 | Battles | | |
| 6,129,964 A * | 10/2000 | Seth | ....................... | C09J 7/0296 24/306 |
| 6,238,623 B1 | 5/2001 | Amhof et al. | | |
| 6,287,031 B1 * | 9/2001 | Willis | ........................ | B41J 2/01 101/227 |
| 6,435,128 B2 | 8/2002 | Qiu et al. | | |
| 6,485,978 B1 | 11/2002 | Kirckof et al. | | |
| 6,790,411 B1 * | 9/2004 | Read | .......................... | A61L 2/28 206/438 |
| 7,014,631 B2 * | 3/2006 | Jackson | ................... | A61F 13/58 428/195.1 |
| 8,083,064 B2 | 12/2011 | Boswell et al. | | |
| 8,323,562 B2 * | 12/2012 | Schorr | ............... | B65D 81/2023 250/453.11 |
| 2001/0023001 A1* | 9/2001 | Weiss | ................... | A61B 19/026 428/35.2 |
| 2005/0092636 A1* | 5/2005 | Su-Syin | .................... | A61L 2/07 206/363 |
| 2005/0255998 A1* | 11/2005 | Taylor | .................. | B41M 5/3333 503/216 |
| 2007/0110925 A1* | 5/2007 | Ridless | ................... | B32B 27/12 428/32.16 |
| 2009/0123332 A1* | 5/2009 | Whitehead | ........... | A61B 19/026 422/27 |
| 2009/0301382 A1 | 12/2009 | Patel | | |
| 2011/0275159 A1 | 11/2011 | Landgrebe et al. | | |
| 2011/0312096 A1 | 12/2011 | Whitman et al. | | |
| 2014/0271345 A1* | 9/2014 | Pavesi | ....................... | A61L 9/00 422/1 |

\* cited by examiner

*Primary Examiner* — Arlen Soderquist
(74) *Attorney, Agent, or Firm* — Dority & Manning, P.A.

(57) ABSTRACT

There is provided a sterilization indicating tape having a breathable and liquid impervious film, wherein the tape is printed with a sterilization indicator ink. The tape is compatible with a wrap polymer for recycling. The tape is used to hold a wrapped package closed so that it can be sterilized and stored. The ink changes color upon sterilization to show the user that the package has been subject to sterilization. The tape is desirably made from the same or a similar polymer to the wrap polymer so that they may be recycled together.

12 Claims, No Drawings

RECYCLABLE INDICATOR TAPE FOR STERILIZATION

This application claims priority from U.S. provisional patent application 61/829,471 filed on May 31, 2013.

The present disclosure relates to an improved tape that may be used in closing packages to be sterilized and that is compatible with the packaging material item so that it may be recycled with it.

Medical materials used in surgery are, of course, required to be in a sterile state for use. Many of these items like forceps, scissors, clamps, scalpels, towels, gowns, drapes and the like are reusable and so need to be sterilized prior to reuse. Some of these items are generally disposable or single use items like surgical gowns and drapes and, unless they are pre-packaged in a sterile state, also need to be sterilized by the hospital prior to their single use.

Hospitals have developed protocols for the collection, cleaning and sterilization of materials to be used in surgery. After surgery, the instruments are gathered and sent for cleaning or laundering as necessary, and then sent to a hospital department responsible for sterilization. Sterilization involves placing the items in a stainless steel instrument tray, wrapping the tray with a "sterilization wrap" and sterilizing the package, generally with steam or ethylene oxide, though other methods of sterilization are also sometimes used. After sterilization, the wrapped instrument tray may be taken directly to surgery for use or may be stored for future use. Storage involves the placement of the wrapped tray on a shelf, or on top of another wrapped tray on shelf, in a storage area of the hospital.

Sterilization wrap is most commonly a nonwoven material that is pliable and lightweight, though woven fabrics such as launderable cotton linen are also occasionally used, though their use is declining due to barrier and cost concerns. Sterilization wrap is more commonly made from low cost polymers like polyolefins, particularly polypropylene and is a single use material that is disposed of or recycled after use.

The sterilization wrap functions by allowing the sterilization gas (e.g. steam or ethylene oxide) to pass through the wrap and contact the interior contents of the wrapped package. It is critical that the sterilization wrap prohibit the passage of microorganisms from the outside of the package to the interior once the wrapped package has been sterilized.

One way to ensure that the package has been wrapped in a sufficiently durable manner is to use a dual layer sterilization wrap. U.S. Pat. No. 5,635,134 to Bourne, et al. discloses a multi-ply sterilization wrap which is formed by joining one or more sheets of sterilization wrap (e.g., two separate sheets or one sheet folded over) together to form two similarly sized, superposed panels that allow convenient dual wrapping of an article. As another example, US patent publication 2001/0036519 by Robert T. Bayer discloses a two ply sterilization wrap that is formed of a single sheet of sterilization wrap material which is folded to form two similarly sized, superposed panels that are bonded to each other. As yet another example, US patent publication 2005/0163654 by Stecklein, et al. discloses a sterilization wrap material that has a first main panel and a second panel that is smaller than the main panel. The second panel is superposed and bonded to the central portion of the main panel such that it is contained entirely within the main panel to reinforce the main panel and/or provide additional absorbency. Still another example is U.S. patent application Ser. No. 12/850,697 that provides a multi-panel sterilization assembly that includes a barrier panel formed of a permeable material, a fold protection panel, and at least one panel attachment means.

Because of the volume of materials that must be sterilized, it is often necessary to sterilize and store these products for use as desired. Accordingly, there has been developed a procedure where such products are packaged in sterilization wrappers (as described above) for subsequent use, and the wrapped package is then sterilized and stored. As may be apparent, there is a potential danger in such a procedure. There is a prospect of unsterilized packages becoming mixed with sterilized packages when stored for use.

To prevent unsterilized products from being used by the physician or attendant requiring sterile materials, various types of sterility indicators that may be attached to, or incorporated into, the wrapped sterilization package have been developed. This permits a user to immediately visually determine whether a particular package has been passed through the sterilizer. Although such sterilization indicators have, in many instances, been placed in the wrapped package or attached to the wrapped package, the most convenient way of applying such sterilization indicators is to have the sterilization indicators carried by adhesive indicator tapes used for holding the wrap in a closed position prior to, during, and after sterilization of the enclosed products. Examples of such tape may be found in U.S. Pat. Nos. 5,460,880 and 5,518,763.

Unfortunately, though prior art tape has been used to hold the packages closed it has been found to be incompatible with the polymeric packaging (or wrap) material for recycling purposes because it is made from a material that must be recycled separately. As a result, wrap and tape that could be have been recycled are disposed of in conventional ways (e.g. in landfills) that produce an unnecessary burden on resources and increase costs. Alternatively, the tape must be completely removed from the wrap and disposed of (or recycled separately), while the wrap is recycled, adding to costs. Furthermore, known film tapes that are compatible with the wrap for recycling do not allow steam or ethylene oxide to pass through them, causing doubts about the thoroughness of the sterilization.

One skilled in the art can recognize that despite the improvements in wrapping packages to be sterilized and the recycling of much of the material, further improvements can be made. In particular, a tape that was compatible with the wrap material so that it could be recycled together with it would reduce the burden on landfills and reduce costs. A successful tape should allow steam and ethylene oxide to pass through it to ensure thorough sterilization and activation of the indicator ink. A successful tape should also indicate to the user whether the wrapped package has been sterilized or not.

SUMMARY

The problems discussed above have found a solution to a large degree in the present disclosure, which describes a multilayer non-woven and film medical indicator tape.

In one embodiment the tape is a breathable, liquid impervious film that is made from a polymer that is compatible for recycling with the wrap material and that can be printed with a sterilization indicator ink.

In another embodiment the tape is a breathable, liquid impervious film that is made from a polymer that is compatible for recycling with the wrap material, and that is laminated on one or both sides to a nonwoven fabric or nonwoven laminate that is compatible for recycling with the wrap material and that can be printed with a sterilization indicator ink.

In another embodiment, the disclosure encompasses packaging materials comprising wrap and tape, in which the wrap and tape are made from polymeric materials that are compatible for recycling, the tape is breathable and liquid impervious and is printed with a sterilization indicator ink.

The basis weight of SMS laminate is desirably between 0.4 and 1.2 osy (13.5 and 40.7 gsm) and more desirably about 0.8 osy (27.1 gsm). The third spunbond desirably has a basis weight between 0.2 and 1.0 osy (6.8 and 33.9 gsm) and more desirably about 0.6 osy (20.3 gsm). The film layer desirably has a basis weight between 0.2 and 1.0 osy and more desirably about 0.6 osy. The overall basis weight of the SMSFS laminate is between about 0.8 osy and 3.2 osy (108.5 gsm), more desirably about 2.0 osy (67.8 gsm). The basis weight of nonwoven fabrics is usually expressed in ounces of material per square yard (osy) or grams per square meter (gsm) and the fiber diameters useful are usually expressed in microns.

The SMS portion of the tape may have its construction skewed so that the first or outer spunbond layer contains between 40 and 80 percent of the basis weight of the laminate. Alternatively, the SMS may have a first spunbond layer that has between 50 and 70 percent of the basis weight of the laminate. The SMS may have a meltblown layer having between 10 and 40 percent of the basis weight of the SMS portion of the tape.

It is required that the polymers used in the layers of multilayer embodiments be compatible for recycling with each other and with the wrap. As an example, it would be inappropriate to use a Teflon® film layer with polyolefin nonwoven layers since they must be separated for recycling.

The film layer is breathable and liquid impervious and yet allows the passage of steam, ethylene oxide or other sterilants. The film generally includes a core layer including a thermoplastic polymer, and a particulate filler. The film also includes two skin layers, one on each side of the core layer. The skin layers each include a thermoplastic polymer and may include particulate filler. The skin layers are desirably used as thermal bonding layers to nonwoven web layers on either side of the film. To this end, the skin layers desirably provide the film with compatible surfaces energy for improved thermal bonding. Specifically, the surface may be oleophilic surfaces, which may permit the passage of oil, such as mineral oil, but do not permit the passage of aqueous liquids through the film. Additionally, the functional additive may be added to skin layers to enhance the surface properties thereby making it more receptive to printing or coating with inks and or adhesive.

Other objects, advantages and applications of the present disclosure will be made clear by the following detailed description of an embodiment of the disclosure.

DETAILED DESCRIPTION

The typical medical fabric material is a nonwoven fabric or web such as a spunbond, meltblown, spunbond polymer laminate in which the layers are usually produced one onto another, resulting in a sandwich with the meltblown layer in the middle. This is generally referred to as "SMS".

The term "polymer" includes, but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries. Other suitable polymers include without limitation thermoplastics, for example polyolefins, polyurethanes, polyamides, polyesters, polyacrylics and co-polymer derivatives and combinations of the foregoing As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, airlaying processes and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

The term "spunbonded fibers" refers to small diameter fibers which are formed by extruding molten thermoplastic polymer material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 20 microns.

The term "meltblown fibers" means fibers formed by extruding a molten thermoplastic polymer material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers which may be continuous or discontinuous, are generally smaller than 10 microns in average diameter, and are generally tacky when deposited onto a collecting surface.

A "multilayer nonwoven laminate" means a laminate wherein some of the layers are spunbond and some meltblown such as a spunbond/meltblown/spunbond (SMS) polymer laminate and others as disclosed in U.S. Pat. No. 4,041,203 to Brock et al., U.S. Pat. No. 5,169,706 to Collier, et al, U.S. Pat. No. 5,145,727 to Potts et al., U.S. Pat. No. 5,178,931 to Perkins et al. and U.S. Pat. No. 5,188,885 to Timmons et al. Such a laminate may be made by sequentially depositing onto a moving forming belt first a spunbond fabric layer, then a meltblown fabric layer and last another spunbond layer and then bonding the laminate. Alternatively, the fabric layers may be made individually, collected in rolls, and combined in a separate bonding step.

It is desirable that nonwoven laminates for use in this disclosure be made in the sequential manner as described above wherein the individual layers are deposited onto a moving forming belt; first a spunbond fabric layer, then a meltblown fabric layer and last another spunbond layer and bonded to form an SMS laminate, for example. As noted above, however, the layers may be made separately, stored for a time in roll form, and unrolled and bonded together to form the laminate in a separate step. In still another alternate method of manufacturing, one or more of the layers (e.g. the spunbond layer) may be made separately and stored as a roll. At a later time the spunbond layer may be unrolled and the other layers (e.g. the meltblown, spunbond) formed and directly deposited onto the spunbond layer.

The basis weight of a suitable SMS polymer laminate is desirably between 0.4 and 1.2 osy (13.5 and 40.7 gsm) and more desirably about 0.8 osy (27.1 gsm). The third spunbond desirably has a basis weight between 0.2 and 1.0 osy (6.8 and 33.9 gsm) and more desirably about 0.6 osy (20.3 gsm). The film layer desirably has a basis weight between 0.2 and 1.0 osy and more desirably about 0.6 osy. The overall basis weight of the SMSFS laminate thus created is between about 0.8 osy and 3.2 osy (108.5 gsm), more desirably about 2.0 osy (67.8 gsm).

The term "film" refers to a thermoplastic film made using a film extrusion process, such as cast, blown film or extrusion coating. This term includes films rendered microporous by mixing polymer with filler, forming a film from the mixture, and stretching the film to create the voids. Additionally, two or more incompatible polymers could be blended and also stretched to create a microporous film. Also included are films in which one or more polymers are extracted by a solvent or other means to create micropores. It also includes monolithic films which rely on the solubility of water molecules in the solid polymer film, the diffusion of water molecules through the solid polymer film and evaporation of the water passing through the film into the surrounding air. In addition, foams with ruptured "cells" from stretching or "open cells" also are included, provided there is a sufficiently tortuous path to prevent the passage of aqueous liquids.

By "compatible" for recycling is meant that the tape and wrap are made from the same or very similar polymers. For example, a polypropylene tape and polypropylene wrap are compatible for recycling. A polyethylene tape and polypropylene wrap are also compatible for recycling. Generally, olefinic polymers are compatible with each other for recycling, different nylons are compatible with each other for recycling, urethanes are compatible with other urethanes, etcetera.

The term "microporous" refers to films having voids separated by thin polymer membranes and films having micropores passing through the films. The voids or micropores can be formed when a mixture of polymer and filler is extruded into a film and the film is stretched, preferably uniaxially in the machine direction. Other methods of producing a microporous film are discussed above under the definition of the term "film". Microporous films tend to have water vapor transmission due to molecular diffusion of water vapor through the membranes or micropores, but substantially block the passage of aqueous liquids (i.e. are liquid impervious).

As used herein, the term "breathable" refers to a material which is permeable to water vapor and has water vapor transmission rate of about 300 $g/m^2/24$ hours to about 1000 $g/m^2/24$ hours.

In one embodiment the tape is a breathable, liquid impervious film that is made from a polymer that is compatible for recycling with the wrap material and that can be printed with a sterilization indicator ink. The core layer of the film can include any suitable film-forming matrix polymer. Examples of suitable matrix polymers include without limitation olefin polymers, for instance polyethylene, polypropylene, copolymers of mainly ethylene and $C_3$-$C_{12}$ alpha-olefins (commonly known as linear low density polyethylene), copolymers of mainly propylene, and flexible polyolefins including propylene-based polymers having both atactic and isotactic propylene groups in the main polypropylene chain. Single-site catalyzed polyolefins are useful, including those described in U.S. Pat. Nos. 5,571,619, 5,322,728, and 5,272,236, the disclosures of which are incorporated herein by reference. In addition to the polymer matrix, the core layer includes a particulate filler discussed above, suitably a particulate inorganic filler. Suitable inorganic fillers include without limitation calcium carbonate, clays, silica, alumina, barium sulfate, sodium carbonate, talc, magnesium sulfate, titanium dioxide, zeolites, aluminum sulfate, diatomaceous earth, magnesium sulfate, magnesium carbonate, barium carbonate, kaolin, mica, carbon, calcium oxide, magnesium oxide, aluminum hydroxide and combinations of these particles. The mean diameter for the inorganic filler particles should range from about 0.1-10 microns, alternatively about 0.5-7.0 microns, alternatively about 0.8-2.0 microns In addition to the core layer, the breathable viral barrier film includes two outer skin layers. Each skin layer includes a polymer matrix. The matrix of the skin layers is preferably formed of a thermoplastic olefin polymer or polymer combination which facilitates thermal bonding of the breathable film to one or more nonwoven webs using a thermal bonding process, such as a calendar bonding process, without compromising the breathability or viral barrier of the film. Suitable skin layer polymers include heterophasic propylene-ethylene copolymers, propylene-ethylene random copolymers, ethylene vinyl acetate, ethylene-methyl acrylate, amorphous (Ziegler-Natta or single-site catalyzed) ethylene-alpha olefin copolymers having densities of about 0.89 grams/$cm^3$ or less, amorphous poly-alpha olefin (APAO) polymers which can be random copolymers or terpolymers of ethylene, propylene and butene, other substantially amorphous or semi-crystalline propylene-ethylene polymers, and combinations of the foregoing.

The film is desirably prepared using a conventional cast co-extrusion process. Once the cast film is prepared, it can be stretched to form around the filler particles in the core and skin layers. The voids are separated by thin polymer membranes, creating a tortuous path for permeability of water vapor but blocking the passage of aqueous and low surface tension liquids. The stretching may be performed in one direction, desirably the machine direction. The stretching may be performed using two or more pairs of nipped draw rollers, with each successive pair turning faster than the preceding pair. One or both draw rollers in each pair may be heated, so that the film experiences a stretching temperature of about 65-100° C. The stretched film may have a thickness of about 2-25 microns, suitably about 5-15 microns, desirably about 7-13 microns.

In the SMSFS embodiment, the third spunbond layer is desirably formed from a polypropylene homopolymer or random propylene-ethylene copolymer including up to 10% by weight ethylene. The polypropylene homopolymer or copolymer may have a melt flow rate (230° C.) of about 2-50 grams/10 min. The spunbond and meltblown layers in the SMS laminate are also desirably formed from a polypropylene homopolymer or random propylene-ethylene copolymer containing up to 10% by weight ethylene, and having a melt flow rate (230° C.) of about 2-50 grams/10 min.

The SMS layer, film and third spunbond layer may be combined in conventional laminate making procedures as discussed above to make a SMSFS laminate. The layers may be adhered to each other using temperature and pressure or may desirably be joined using a small amount of adhesive. For example the spunbond, meltblown, spunbond (SMS) polymeric laminate may be joined to the film (F) polymeric layer which can in turn be joined to the third spunbond (S) polymeric layer to form an SMSFS laminate. In cases were adhesive is used to join the layers, the amount of adhesive has been found to be equivalent to about 0.02 osy (0.7 gsm) total for both sides of the film. The adhesive is not believed to be present in a quantity that would interfere with the recycling of the tape and wrap.

In like manner, if only one side of the film layer is attached to a nonwoven layer (e.g. a spunbond layer) it may be adhesively joined as described above. If nonwoven layers are attached to both sides of the film layer, adhesive may be applied between the film and both nonwovens. In this manner the tape may be a SFS, SF, SFM, FM, SMSFS, SMSFSMS, SMFS or other combination of nonwoven and film layers.

The ink may be applied to the outermost layer (the layer farthest from the package to be sterilized) by known means such as ink jet printing, melt spraying, and other means. Indicator inks change color, typically from yellow to brown or colorless to black, upon sterilization. Such inks are commercially available from a number of sources, including Shield Sterilization and Packaging Co. Ltd of Anhui, China and Namsa® of Northwood, Ohio and are heavy metal (e.g. lead) free. The ink is not believed to be present in a quantity that would interfere with the recycling of the tape and wrap.

After the laminate has been produced it can be slit into tape of appropriate size by conventional means as desired. Common widths for tape for this use are 0.5 inches (1.27 cm) up to 2.5 inches (6.35 cm), though the width is only limited by the size of the equipment available. Before or after slitting an adhesive is applied to the first spunbond polymer layer. This adhesive is used to attach the tape to the wrap. This adhesive is a conventional pressure sensitive adhesive that will allow the tape to be removed from at least a portion of the wrap to that the package may be opened and the contents removed. The adhesive is not believed to be present in a quantity that would interfere with the recycling of the tape and wrap. An exemplary adhesive is a butyl rubber adhesive.

If the tape is wound into a roll form, the core may be made from the same polymer as the tape or the wrap (e.g. polypropylene) so that the core may also be recycled.

As used herein and in the claims, the term "comprising" is inclusive or open-ended and does not exclude additional unrecited elements, compositional components, or method steps.

While the disclosure has been described in detail with respect to specific embodiments thereof, it will be apparent to those skilled in the art that various alterations, modifications and other changes may be made to the disclosure without departing from the spirit and scope of the present disclosure. It is therefore intended that the claims cover all such modifications, alterations and other changes encompassed by the appended claims.

I claim:

1. A sterilization indicating tape comprising a breathable and liquid impervious film, wherein said film comprises a core layer including a thermoplastic polymer and a particulate filler, wherein said tape is printed with an indicator ink and wherein said tape is compatible with a wrap polymer, wherein said tape and said wrap polymer are recyclable, wherein said film has a first side and a second side, wherein said film is joined on to a nonwoven spunbond layer on the first side, the second side, or both.

2. The tape of claim 1, wherein said ink indicates sterilization by ethylene oxide or steam.

3. The tape of claim 1, wherein said film has a basis weight between 0.2 and 1.0 osy (6.8 and 33.9 gsm).

4. The tape of claim 1, wherein said film has a basis weight of about 0.6 osy (20.3 gsm).

5. The tape of claim 1, wherein said film comprises polypropylene.

6. The tape of claim 1, wherein said film comprises polyethylene.

7. The tape of claim 1, wherein said thermoplastic polymer includes an olefin polymer.

8. The tape of claim 1, wherein said film further includes a first outer skin layer and a second outer skin layer, wherein the first outer skin layer, the second outer skin layer, or both include a thermoplastic polymer.

9. The packaging material of claim 8, wherein said thermoplastic polymer includes an olefin polymer.

10. The packaging material of claim 8, wherein said particulate filler has a mean diameter of from about 0.1 microns to about 10 microns.

11. The tape of claim 1, wherein said particulate filler has a mean diameter of from about 0.1 microns to about 10 microns.

12. A packaging material comprising a wrap and tape, wherein said wrap and tape are made from polymeric materials that are compatible and recyclable, wherein said tape comprises a breathable and liquid impervious film, wherein said film comprises a core layer including a thermoplastic polymer and a particulate filler, wherein said film has a first side and a second side, wherein said film is joined on to a nonwoven spunbond layer on the first side, the second side, or both, and wherein said tape is printed with a sterilization indicator ink.

* * * * *